(12) United States Patent
Baghdassarian

(10) Patent No.: US 6,582,376 B2
(45) Date of Patent: Jun. 24, 2003

(54) ALVEOLAR BREATH COLLECTION DEVICE AND METHOD

(75) Inventor: Ohan Baghdassarian, Glendale, CA (US)

(73) Assignee: Pranalytica, Inc., Santa Monica, CA (US)

(*) Notice: Subject to any disclaimer, the term of this patent is extended or adjusted under 35 U.S.C. 154(b) by 18 days.

(21) Appl. No.: 09/953,225

(22) Filed: Sep. 13, 2001

(65) Prior Publication Data

US 2003/0050567 A1 Mar. 13, 2003

(51) Int. Cl.[7] .............................. A61B 5/08; B65D 81/00
(52) U.S. Cl. ................. 600/543; 600/532; 600/529; 73/23.3
(58) Field of Search ................. 600/529, 532, 600/543; 73/863.01–863.03, 863.11, 863.12, 863.21

(56) References Cited

U.S. PATENT DOCUMENTS

| | | | | |
|---|---|---|---|---|
| 3,321,976 A | | 5/1967 | Jones | 600/543 |
| 3,661,528 A | * | 5/1972 | Falk | 73/863.01 |
| 3,858,573 A | | 1/1975 | Ryan et al. | |
| 4,221,224 A | * | 9/1980 | Clark | 600/531 |
| 4,248,245 A | * | 2/1981 | Kempin | 600/532 |
| 4,297,871 A | | 11/1981 | Wright et al. | 73/23 |
| 5,361,772 A | | 11/1994 | Murnick et al. | 600/543 |
| 5,432,094 A | | 7/1995 | Delente | 436/127 |
| 5,465,728 A | * | 11/1995 | Phillips | 600/543 |
| 5,632,281 A | | 5/1997 | Rayburn | |
| 6,360,582 B1 | * | 3/2002 | Chelvayohan et al. | 73/23.2 |

* cited by examiner

Primary Examiner—Robert L. Nasser
Assistant Examiner—Patricia Mallari
(74) Attorney, Agent, or Firm—Jones Day (57) ABSTRACT

A device for collecting alveolar breath. Breath is expired into the inlet of a hollow body. The hollow body has two outlets, with a valve disposed in each outlet. The concentration of a specific gaseous component of expired breath is monitored by a gas concentration monitor as the expired breath passes through the hollow body to determine when alveolar breath is present in the hollow body. When alveolar breath is present in the hollow body, the valve in the second outlet is actuated to an open position to collect the alveolar breath in the collection reservoir affixed to the hollow body at the second outlet.

19 Claims, 5 Drawing Sheets

ALVEOLAR BREATH COLLECTION DEVICE AND METHOD

BACKGROUND OF THE INVENTION

1. Field of the Invention

The field of the present invention is devices and methods relating to the collection of alveolar breath.

2. Background

Most human adults have a lung capacity of approximately 5–6 liters. Of this capacity, approximately only 0.3 liters is involved with the exchange of gases between blood and breath which takes place in the alveoli. Within this 0.3 liters, called the alveolar breath, oxygen and carbon dioxide rapidly diffuse across the epithelial membrane separating blood from breath due to concentration gradients existing between the blood and breath. As a result, the concentration of many gaseous constituents in the alveolar breath closely reflect the partial pressure of the same constituents in blood or reflect the presence of surrogates in blood from which the gas is derived.

Also present in alveolar breath are trace concentrations of molecules which are small enough to diffuse through the epithelial membrane. Some of these molecules have been shown to be indicative of disorders such as diabetes, lung cancer, renal failure, and asthma. Furthermore, depending on the severity of the disorder, such molecules may be present in alveolar breath in the parts per billion range (ppb) or in the parts per trillion range (ppt). Measurement of these trace components is therefore desirable for the early diagnosis of these disorders.

However, consistently collecting undiluted alveolar breath samples has proven to be a difficult task. During respiration, of the six liter total lung capacity, only 0.5 liters (called the tidal volume) is exchanged with the ambient atmosphere. However, this 0.5 liters is not the only constituent of a normally expired breath. The first part of expired breath consists essentially of air disposed in the mouth, nose, and upper respiratory tract. The next part of expired breath consists essentially of air from the bronchi and lower respiratory tract. Neither of these first two parts of expired breath exchange gases with blood. Therefore, the concentration of a particular gas in either of these two parts does not necessarily reflect blood content of that gas. The third and last part of expired breath consists essentially of alveolar breath.

Many devices exist in the prior art to collect alveolar breath samples. However, such devices tend to rely upon various different assumptions about breathing patterns to collect the alveolar breath sample. Unfortunately, these assumptions may lead to the collection alveolar breath samples which are diluted or the collection of breath samples which do not contain any alveolar breath.

For example, the device disclosed in U.S. Pat. No. 3,858,573 relies on the volume of a gas trap reservoir and the air pressure of an expired breath to capture an alveolar breath sample. The '573 device consists of a gas trap reservoir having pressure sensitive valves enclosing each end, one acting as an inlet and the other acting as an outlet. Breath is expired through the inlet valve, with the pressure of the expired breath displacing any gas or breath inside the gas trap reservoir and forcing it through the outlet valve. This gas displacement continues until the breath is completely expired. Alveolar breath, being the last part of the expired breath, is trapped in the reservoir. The '573 device and others like it rely on the assumption that alveolar breath is always expired. However, if the full tidal volume of breath is not expired, then alveolar breath either is never expired or is only partially expired. Thus, at times a partial alveolar breath sample is collected, such a partial sample being diluted with non-alveolar breath, or no alveolar breath is collected because none was actually expired. U.S. Pat. No. 5,211,181 discloses a device which is different from the '573 device, but relies on the same assumptions about expired breath to collect an alveolar breath sample.

Another device for collecting an alveolar breath sample is disclosed in U.S. Pat. No. 5,361,772. This device consists of a small collection chamber with caps on each open end that are manually actuated to close the openings and trap an alveolar breath sample. The '772 device relies on the small size of the chamber and the displacement of breath as it is expired through the chamber to trap alveolar breath. However, in many instances the '772 device may be undesirable because it requires manual actuation to trap the alveolar breath sample. Therefore, the individual actuating the device, who may be different from the individual exhaling into the device, must necessarily guess as to when the expired breath consists of alveolar breath. The result of such a required method of operation is that an undiluted alveolar breath sample may not always be trapped in the collection chamber.

Yet another device used to collect an alveolar breath sample is disclosed in U.S. Pat. No. 4,297,871. This device monitors the flow rate of expired breath as it passes through part of the device. When the flow rate drops below specified threshold, the alveolar breath sample is drawn into a reservoir for analysis. The '871 device operates on the assumption that when the flow rate of an expired breath drops below a predefined value, alveolar breath is present to be collected. Such an assumption, however, does not take into account normal variations in breathing patterns. For example, if breathing is stopped midway through an exhale, the device will sense a decrease in air flow and collect a breath sample. Under these circumstances, the breath sample collected will likely consist of either diluted alveolar breath or non-alveolar breath.

Thus, because of shortcomings in the prior art devices, an improved alveolar breath collection device is needed which can repeatedly and reliably collect an undiluted alveolar breath sample every time alveolar breath is expired. Such a device should be capable of adapting to the breathing patterns among different individuals and the breathing patterns of a single individual over the period of several breaths.

SUMMARY OF THE INVENTION

The present invention is directed to a device and method for collecting alveolar breath. The alveolar collection device comprises a hollow body having an inlet and two outlets. A first valve is disposed in the first outlet and a second valve is disposed in the second outlet. A collection reservoir is affixed to the hollow at the second outlet. A gas concentration monitor is operatively affixed to the hollow body to monitor the concentration of a specific gaseous component in expired breath passing through the hollow body. When the concentration of the specific gaseous component indicates that alveolar breath is present in the hollow body, the monitor actuates the second valve to an open position.

In practicing the method of this invention, expired breath is passed into the hollow body through the inlet and out of the hollow body through the first valve disposed in the first outlet. The concentration level of a specific gaseous component is monitored as the expired breath passes through the hollow body to determine when alveolar breath is present in the hollow body. When alveolar breath is present in the hollow body, the second valve, which is disposed in the second outlet, is actuated to divert the alveolar breath out of the hollow body and into a collection reservoir.

Thus, in a first separate aspect of the present invention, the alveolar collection device comprises a hollow body having an inlet, a first outlet with a first valve disposed therein, and a second outlet with a second valve disposed therein. A collection reservoir is affixed to the hollow body at the second outlet. A gas concentration monitor is operatively affixed to the hollow body to monitor the concentration of a specific gaseous component of expired breath. When the concentration of the specific gaseous component indicates that alveolar breath is present in the hollow body, the monitor actuates the third valve to an open position, thus collecting the alveolar breath in the collection reservoir.

In a second separate aspect of the present invention, the monitor compares the concentration of the specific gaseous component to a predetermined threshold concentration to determine when alveolar breath is present in the hollow body In a third separate aspect of the present invention, the first valve comprises a one-way pressure sensitive valve.

In a fourth separate aspect of the present invention, the second valve is biased in the closed position.

In a fifth separate aspect of the present invention, heating elements are disposed on one or more surfaces of the hollow body to prevent the condensation of the expired breath passing through the hollow body.

In a sixth separate aspect of the present invention, a third valve is disposed in the inlet, the third valve being a one-way pressure sensitive valve.

In a seventh separate aspect of the present invention, the collection reservoir is detachably affixed to the hollow body.

In an eighth separate aspect of the present invention, any of the foregoing aspects may be employed in combination.

Accordingly, it is an object of the present invention to provide an improved apparatus and method for collecting an alveolar breath sample. Other objects and advantages will appear hereinafter.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
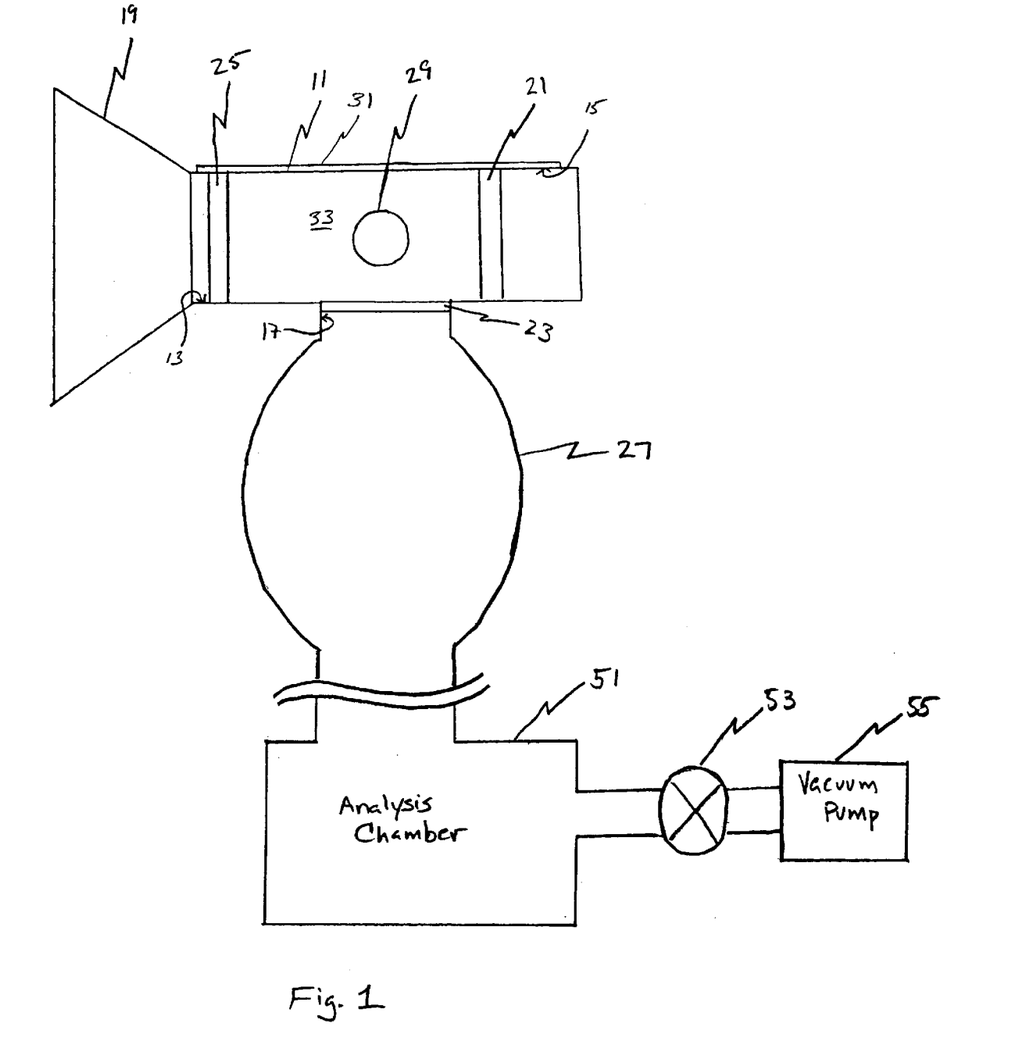
FIG. 1 is a side sectional view of an alveolar breath collector in accordance with the preferred embodiment.

Turning in detail to the drawings, FIG. 1 illustrates an alveolar breath collector according to the preferred embodiment of the invention. A hollow body 11 has At an inlet 13 and two outlets 15, 17. The material from which the hollow body 11 is constructed is preferably one which is inert to and will not absorb or adsorb the molecules in expired breath passing through it. Teflone® PFA and quartz are examples of materials having such qualities.

A first valve 23 is disposed in the first outlet 15, a second valve 25 is disposed in the second outlet 25, and a third valve 21 is disposed in the inlet 13. A sampling chamber 33 is thus formed in the interior volume of the hollow body, the sampling chamber 33 being defined by the first, second, and third valves. Alveolar breath is detected within and collected from the sampling chamber 33. In order to enable the collection of an undiluted alveolar breath sample, the collector is constructed so that the sampling chamber 33 has a volume that is less than the volume of alveolar breath expired by an average adult individual. Preferably, the volume of the sampling chamber 33 is approximately 150 ml. The collector may also be constructed so that the volume of the sampling chamber 33 is less than the volume of alveolar breath expired by children, including infants.

The presence of dead space in the sampling chamber 33, or space in which little or no air flow occurs when expired breath passes through the collector, can contribute to dilution of a collected alveolar breath sample. Additionally, any cavity integrally connected to the sampling chamber 33 may also create undesirable dead space. Dead space, however, may be reduced through design implementations, some of which are incorporated into the collector illustrated in FIG. 1. One design implementation is the inclusion of the third valve at the inlet. This third valve 25 divides the space between the sampling chamber 33 and the mouth of the individual breathing into the collector. Without the third valve 25 in the inlet, the mouth of the individual expiring through the collector becomes an extension of the sampling chamber 33, effectively increasing the volume of the sampling chamber 33. However, by including the oral cavity is included as part of the sampling chamber 33, more dead space may be introduced to the system.

Another design implementation is the placement of the first valve 21 near the second outlet 17. By placing the first valve 21 thusly, potential dead space between the second outlet 17 and the first outlet 15 is eliminated when collecting the alveolar breath sample through the second outlet 17. Additionally, the second valve 23 is placed near the interior opening of the second outlet 17 to reduce dead space when breath is exiting the hollow body 11 through the first outlet 15. Yet another design implementation is to construct the interior walls of the hollow body so that they are relatively smooth, as doing so avoids creating many small pockets of dead space. Other design implementations which decrease dead space in the collector may become apparent to those skilled in the art as the collector is used in practice.

The first and third valves 21, 25 are preferably one-way, non-rebreathing check valves which are sensitive to low pressure differentials, such valves being readily available through commercial sources, such as Harvard Apparatus of Holliston, Mass. Preferably, the first and third valves 21, 25 will open with pressure differentials of less than approximately 10 mm Hg, and more preferably less than approximately 5 mm Hg, and even more preferably less than approximately 1 mm Hg. Additionally, the first and third valves 21, 25 are preferably not gravity dependent and have excellent elastic memory to avoid deformation over time. The first valve 21 may optionally be a non-pressure sensitive valve that is actuated to a closed position when an alveolar breath sample is collected and maintained in an open position at all other times.

The second valve 23 is preferably biased in the closed position so that expired breath passes through the second outlet 17 only when the second valve 23 is actuated to an open position. Alternatively, the second valve 23 may be maintained in a closed position until it is actuated to an open position.

A mouthpiece 19 is affixed to the hollow body 11 at the inlet 13. The mouthpiece 19 is large enough to cover an individual's mouth and preferably constructed of a pliant material, thus allowing it to form fit to the face. The mouthpiece 19 may optionally be constructed to cover an individual's mouth and nose, or just an individual's nose. The mouthpiece 19 is removable to allow for easy cleaning and to allow different sizes to be used with the collector. Additionally, having a removable mouthpiece permits the collector to be attached to and used in conjunction with artificial breathing or breathing assistance apparatuses.

Heating elements 31 are integrated into the side walls of the hollow body 11 to heat the hollow body 11 and prevent expired breath from condensing on it's interior walls. Without the heating elements, the hollow body 11 may be much cooler than the expired breath, leading to the condensation of the water content in expired breath on the hollow body 11. Once the water content begins to condense, other molecules in the expired breath may be dissolved into the condensate. Any subsequent analysis of a collected alveolar breath sample, therefore, will not reflect the actual content of the expired breath because of the constituents left behind in the condensate.

Figure 2:
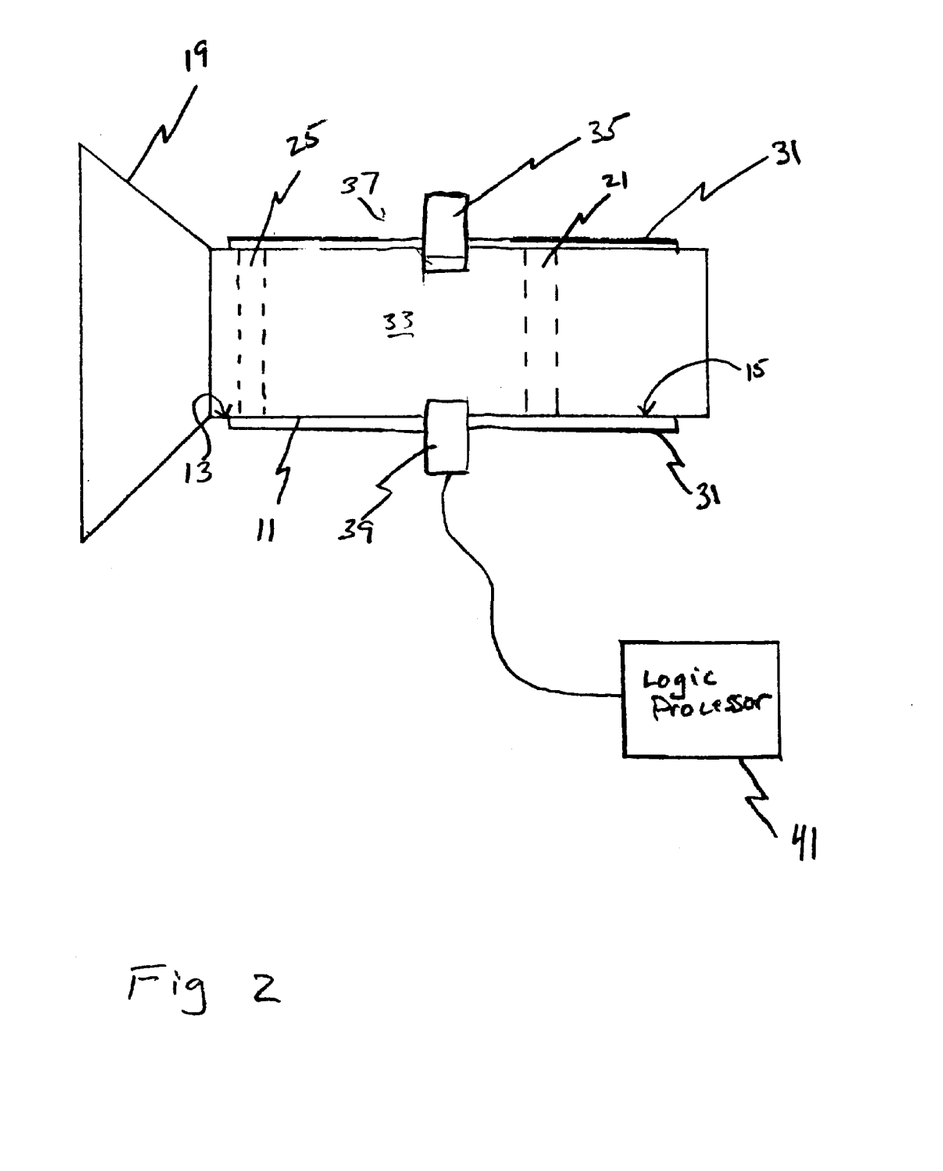
FIG. 2 is a top view of the alveolar breath collector of FIG. 1.

A gas concentration monitor 29 is operatively affixed to the hollow body 11 to monitor the concentration of a specific gaseous component of expired breath as the expired breath passes through the sampling chamber 33. In FIG. 2, the gas concentration monitor 29 is shown disposed partially within the sampling chamber 33. However, the monitor may be disposed wholly within or without the sampling chamber 33 so long as its positioning does not impede its monitoring function. Additionally, the gas concentration monitor 29 may comprise any detector known to those skilled in the art which enables the a concentration measurement of a gaseous component. For example, an infrared lamp detector may be used or a detector employing an infrared laser, such as the detectors disclosed in U.S. patent application Ser. No. 09/812,067, filed on Mar. 19, 2001, the disclosure of which is incorporated herein by reference. The gas concentration monitor 29 is in communication with the second valve 23 such that the monitor 29, may actuate the second valve 23 to an open position. The process by which the monitor 29 actuates the second valve 23 is further described below.

A collection reservoir 27 is affixed to the hollow body 11 at the second outlet 17 so that when the second valve 23 is actuated to an open position, the interior of the reservoir 27 is in communication with the sampling chamber 33. An analysis chamber 51, a valve 53, and a vacuum pump 55 are sequentially communicably connected to the reservoir 27. The vacuum pump 55 and the valve 53 are used to maintain the pressure in the reservoir 27 at less than atmospheric pressure. Preferably, the reservoir 27 is maintained at approximately two-thirds of an atmosphere. By maintaining a pressure differential between the sampling chamber 33 and the reservoir 27, alveolar breath is drawn out of the sampling chamber 33 and into the reservoir 27 when the second valve 23 is opened. The pressure differential also serves to draw the alveolar breath from the reservoir 27 and into the analysis chamber 51 where it may be analyzed for diagnostic purposes.

A dynamic analysis system is established by using the vacuum pump 55 to draw the alveolar breath sample from the sampling chamber 33, through the collection reservoir, and into the analysis chamber 51. Depending upon the analysis being performed on the alveolar breath sample, a dynamic system may be preferred over a static analysis system, such as is described below in association with FIG. 5. In a dynamic system the alveolar breath sample is kept in constant motion by the vacuum pump 55, leaving the molecules in the sample with little opportunity to adhere to surfaces. In a static system, the lack of motion allows molecules in the sample, such as ammonia, the opportunity to adhere to surfaces, and molecules which have adhered to surfaces may avoid the analysis process if the process is focused solely on the gaseous portion of the sample.

In operation, breath is expired into the collector and the concentration of the specified component in the expired breath is monitored. In the following example, the gas concentration monitor 29 comprises an infrared lamp detector. As illustrated in FIG. 2, the infrared lamp detector comprises an infrared lamp 35, a wavelength selector 37, and a light detector 39. Light from the infrared lamp is directed through the wavelength selector 37, into the sampling chamber 33, and towards the light detector 39 which measures the power of the light. The wavelength selector is chosen to pass only a predetermined wavelength which corresponds to an absorption peak of the specified component.

The light detector 39 periodically measures the power of the light as the expired breath passes through the sampling chamber 33. The sampling rate of the detector 39 may be adjusted to achieve the desired sensitivity of the gas concentration monitor 29. Preferably, the power of the light is sampled approximately once every one-tenth of a second. Alternatively, the sampling rate may be made dependent on the breathing rate of the individual breathing into the collector. For example, during a first expiration into the collector, the individual's breathing rate, based on a single exhale and inhale, is measured. Thereafter, for each subsequent breath the sampling rate is a predetermined fraction of the measured breath rate. Additionally, the breath rate of each subsequent breath may be continually monitored, thus allowing the sampling rate to be adjusted for each breath. In this manner, the collector may adapt over time to the breathing patterns of an individual.

The power of the light measured at the detector is converted into a concentration measurement by the logic processor 41 component of the gas concentration monitor 29. In FIG. 2, the logic processor 41 is shown as a separate component. However, the logic processor 41 may be integrated with the other components of the gas concentration monitor 29. Converting the power measurement into a concentration of the specified component requires initializing the logic processor 41 by taking power measurements when the sampling chamber does not contain expired breath and when the sampling chamber contains a known concentration of the specified component. Once the logic processor 41 is initialized, the concentration of the specified component in expired breath is determined according to the following equation:

$$Concentration = constant * \frac{P_0 - P_1}{P_0},$$

where $P_0$ is the power measurement when the sampling chamber does not contain expired breath and $P_1$ is the power measurement when expired breath is passing through the sampling chamber. The constant term is determined by using the power measurement from the known concentration and solving for the constant.

Figure 3:
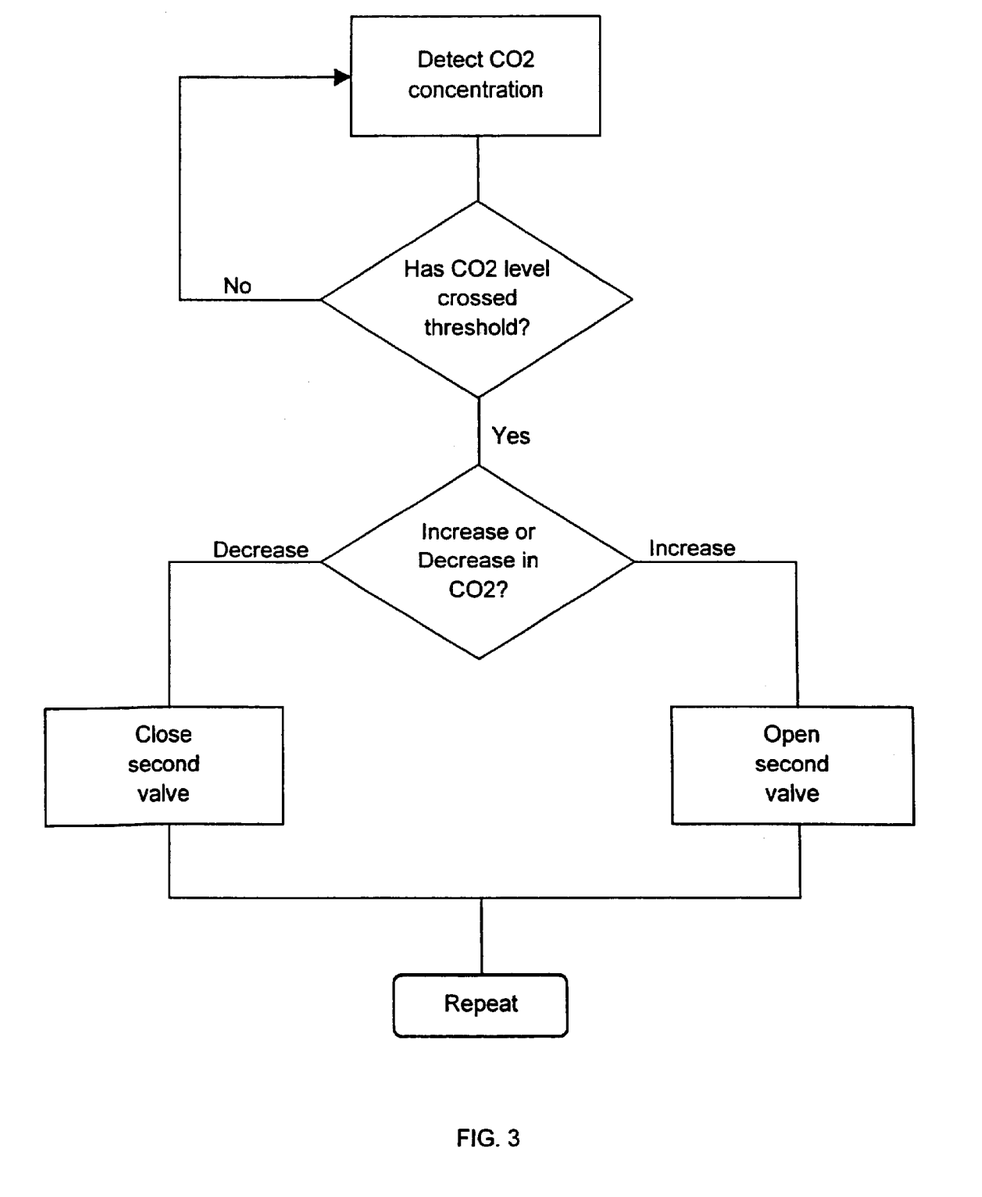
FIG. 3 is a logic diagram showing the operational process of the logic processor in conjunction with the gas concentration monitor.

FIG. 3 is a logic diagram representing the process performed by the gas concentration monitor 29 during operation. As breath is expired through the collector, the concentration of the specified gaseous component is monitored by the process previously described. For each sample taken by the light detector 39, the logic processor 41 determines a present value for the concentration of the specified component.

Figure 4:
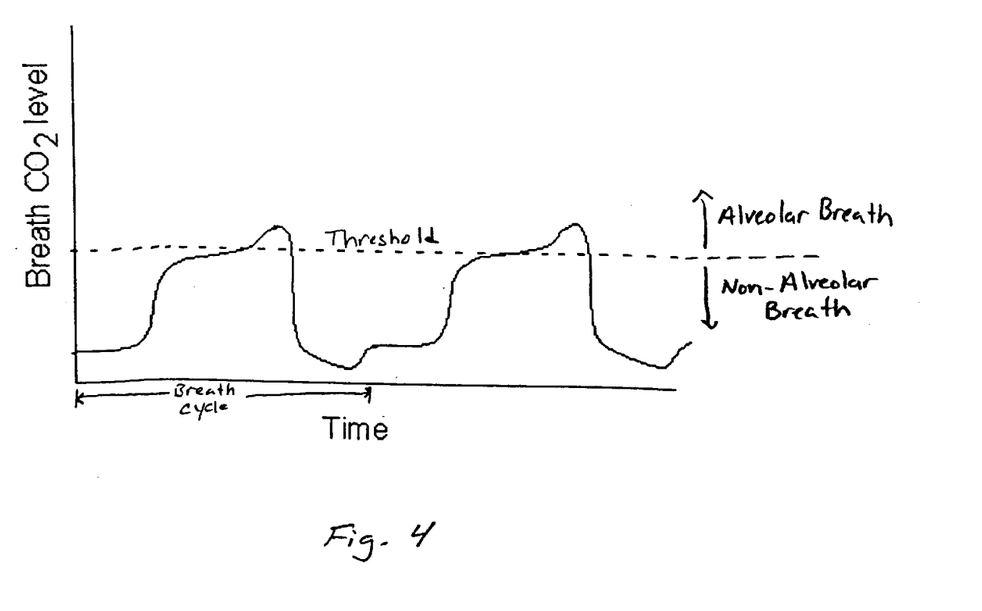
FIG. 4 is a graphical approximation of the carbon dioxide content in expired breath over time.

FIG. 4 graphically represents an approximation of the concentration of carbon dioxide in expired breath over time. Alveolar breath is approximately represented in FIG. 4 at the points where the concentration level passes above the threshold represented by the dashed line. This threshold between non-alveolar breath and alveolar breath is likely to vary from person to person, but it is approximately in the range of carbon dioxide concentrations amounting to 3.5%–5.5% of the expired breath and can be set at an appropriate level for different individuals.

The logic processor 41 compares the present value of the concentration to the predetermined threshold to determine if alveolar breath is present in the hollow body 11. When alveolar breath is present, the gas concentration monitor actuates the second valve to an open position. Conversely, when alveolar breath is no longer present, the second valve is actuated to a closed position.

When carbon dioxide is being monitored, alveolar breath is present in the sampling chamber 33 when the concentration of carbon dioxide becomes greater than the threshold and alveolar breath is no longer present when the carbon dioxide concentration drops back below the threshold. If the specified component is water vapor, then the same would hold true because water vapor in expired breath has a concentration curve which is similar to carbon dioxide. However, the concentration curve for oxygen in expired breath is roughly the inverse of the carbon dioxide concentration curve. Therefore, when the concentration of oxygen drops below the threshold, alveolar breath is present, and when the concentration of oxygen rises above the threshold alveolar breath is no longer present.

Once the monitor determines whether alveolar breath is present, the logic processor 41 actuates the second valve 23 appropriately. For example, as elevated levels of carbon dioxide are detected above the threshold, the second valve is opened and alveolar breath is drawn into the collection chamber. After the concentration drops below the threshold level, the second valve is closed. The process may be repeated for successive breaths.

Figure 5:
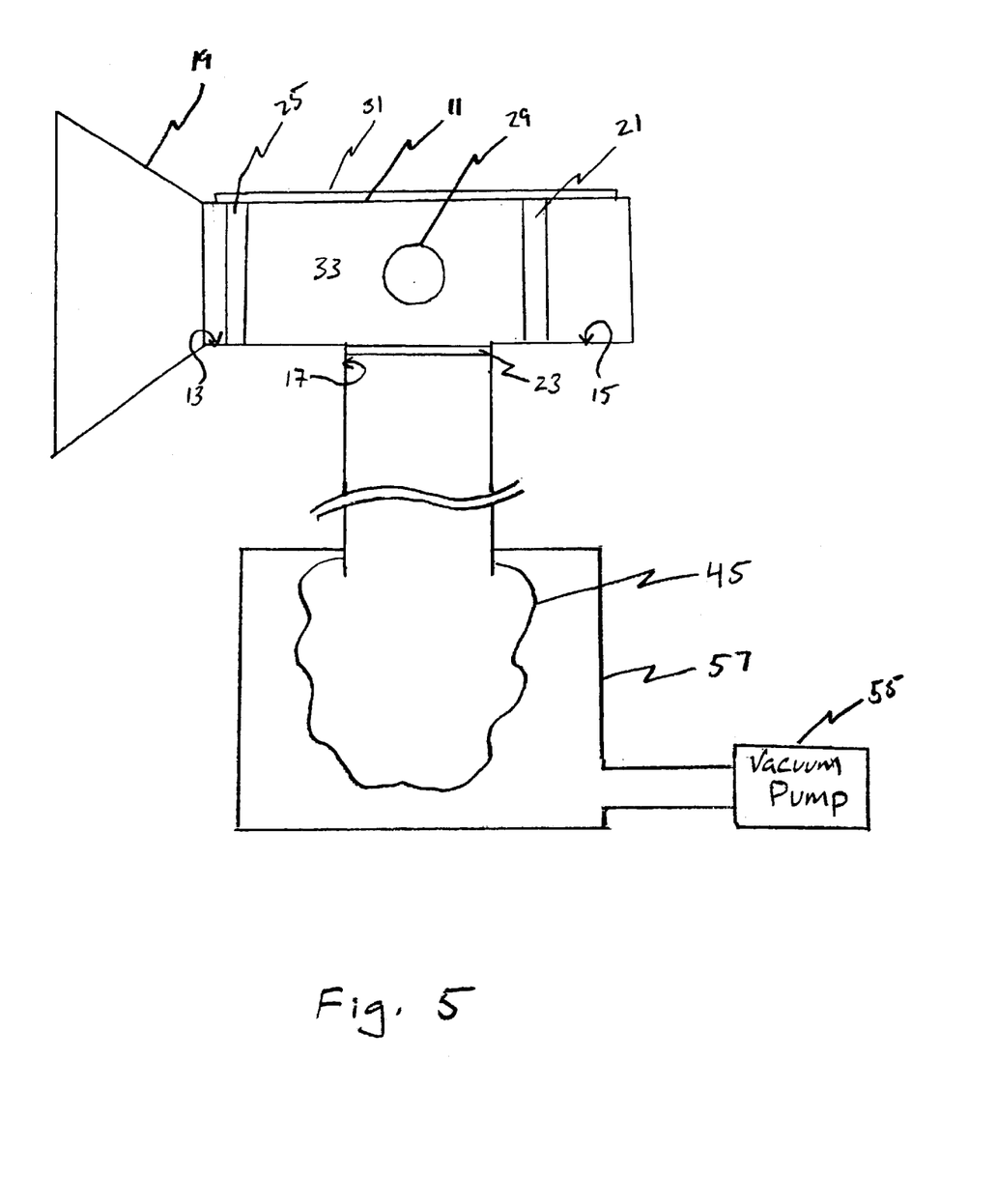
FIG. 5 is a side view of an alveolar breath collector in accordance with an alternative embodiment.

FIG. 5 illustrates an alveolar breath collector having a static collection reservoir. The collection reservoir in FIG. 5 comprises a specimen bag 45 affixed to the second outlet 17. The specimen bag 45 is enclosed in a sealed vacuum chamber 57 which is maintained at less than atmospheric pressure by the vacuum pump 55. Therefore, when the gas concentration monitor 29 actuates the second valve to an open position, the alveolar breath in the sampling chamber 33 is drawn into the specimen bag 45 by the pressure differential. Once the alveolar breath sample is collected, it may be transported in the specimen bag to the appropriate analysis equipment.

Additionally, by configuring the gas concentration monitor in this manner, the concentrations of different molecules in expired breath may be used as a markers for the presence of alveolar breath.

Thus, an alveolar breath collection device and method are disclosed. While embodiments of this invention have been shown and described, it would be apparent to those skilled in the art that many more modifications are possible without departing from the inventive concepts herein. The invention, therefore, is not to be restricted except in the spirit of the following claims.

What is claimed is:

1. A device for collecting alveolar breath comprising:
   a hollow body having an inlet, a first outlet, and a second outlet, wherein a first valve is disposed in the first outlet and a second valve is disposed in the second outlet;
   a collection reservoir affixed to the hollow body at the second outlet;
   a light detection gas concentration monitor operatively connected to the hollow body to monitor a concentration of a specific gaseous component of expired breath and determine when alveolar breath is present in the hollow body based upon the concentration of the specific gaseous component according to the following equation, using an experimentally derived constant:

$$Concentration = constant * \frac{P_0 - P_1}{P_0},$$

where $P_0$ is the power measurement when the sampling chamber does not contain expired breath and $P_1$ is the power measurement when expired breath is passing through said collection reservoir, wherein the monitor actuates the second valve to an open position when alveolar breath is present in the hollow body.

2. The device of claim 1, wherein the gas concentration monitor compares the concentration of the specific gaseous component to a predetermined threshold concentration to determine when alveolar breath is present in the hollow body.

3. The device of claim 1, wherein the first valve comprises a one-way pressure sensitive valve.

4. The device of claim 1, wherein the second valve is biased in the closed position.

5. The device of claim 1, wherein the hollow body includes integrated heating elements.

6. The device of claim 1 further comprising a third valve disposed in the inlet, the third valve being a one-way pressure sensitive valve.

7. The device of claim 1, wherein the collection reservoir is detachably affixed to the hollow body.

8. A method for collecting alveolar breath comprising:
   expiring breath into a hollow body measuring the power when said hollow body does not contain expired breath, measuring the power when expired breath is passing through said hollow body, and determining concentration of a specific gaseous component according to the following equation, using an experimentally derived constant:

$$Concentration = constant * \frac{P_0 - P_1}{P_0},$$

where $P_0$ is the power measurement when the sampling chamber does not contain expired breath and $P_1$ is the power measurement when expired breath is passing through said collection reservoir through an inlet and out of the hollow body through a first valve disposed in a first outlet;
   monitoring a concentration of a specific gaseous component of the breath to determine when alveolar breath is present in the hollow body;

actuating a second valve disposed in a second outlet of the hollow body to an open position when alveolar breath is present in the hollow body to divert the alveolar breath out of the hollow by and into a collection reservoir.

9. The method of claim 8, wherein the concentration of the specific gaseous component is compared to a predetermined threshold concentration to determine when alveolar breath is present in the hollow body.

10. The method of claim 8, wherein the first valve comprises a pressure sensitive valve.

11. The method of claim 8, wherein the second valve biases in the closed position.

12. The method of claim 8, wherein the collection reservoir detachably affixes to the hollow body.

13. The method of claim 8 further comprising heating the hollow body to prevent condensation of the expired breath in the hollow body.

14. A method for collecting alveolar breath comprising:

expiring breath into a hollow body measuring the power when said hollow body does not contain expired breath, measuring the power when expired breath is passing through said hollow body, and determining concentration of a specific gaseous component according to the following equation, using an experimentally derived constant:

$$Concentration = constant * \frac{P_0 - P_1}{P_0},$$

where $P_0$ is the power measurement when the sampling chamber does not contain expired breath and $P_1$ is the power measurement when expired breath is passing through said collection reservoir through an inlet and out of the hollow body through a first valve disposed in a first outlet;

taking successive absorption measurements of a specific gaseous component of the breath in the hollow body;

determining when alveolar breath is present in the hollow body from the successive absorption measurements;

actuating a second valve disposed in a second outlet to an open position when the alveolar breath is present in the hollow body to divert the alveolar breath out of the hollow body and into a collection reservoir.

15. The method of claim 14, wherein determining when alveolar breath is present in the hollow body includes determining a concentration of the specific gaseous component from the successive absorption measurements and comparing the concentration to a predetermined threshold concentration.

16. The method of claim 14, wherein the first valve comprises a pressure sensitive valve.

17. The method of claim 14, wherein the second valve biases in the closed position.

18. The method of claim 14, wherein the collection reservoir detachably affixes to the hollow body.

19. The method of claim 14 further comprising heating the hollow body to prevent condensation of the expired breath in the hollow body.

* * * * *